(12) United States Patent
Tam

(10) Patent No.: US 6,693,081 B2
(45) Date of Patent: *Feb. 17, 2004

(54) BONE STIMULATING FACTOR

(75) Inventor: Cherk Shing Tam, Oakville (CA)

(73) Assignee: Osteopharm Inc., Oakville (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/229,304

(22) Filed: Jan. 13, 1999

(65) Prior Publication Data

US 2002/0090671 A1 Jul. 11, 2002

Related U.S. Application Data

(63) Continuation-in-part of application No. 09/048,058, filed on Mar. 26, 1998, now abandoned, which is a continuation of application No. PCT/CA96/00653, filed on Sep. 26, 1996, now abandoned.
(60) Provisional application No. 60/004,314, filed on Sep. 26, 1995.

(51) Int. Cl.⁷ .......................... A61K 38/08; C07K 7/06; C07K 1/107

(52) U.S. Cl. ......................... 514/16; 530/328; 530/345; 530/380; 530/402

(58) Field of Search ................................ 530/300, 329, 530/328, 327, 326, 325, 324, 380, 345, 402; 514/16, 15, 14, 13, 12

(56) References Cited

U.S. PATENT DOCUMENTS

| | | |
|---|---|---|
| 4,320,118 A | 3/1982 | White et al. |
| 4,877,864 A | 10/1989 | Wang et al. |
| 4,897,348 A | 1/1990 | Johnston et al. |
| 5,011,691 A | 4/1991 | Oppermann et al. |
| 5,024,841 A | 6/1991 | Chu et al. |
| 5,264,214 A | 11/1993 | Rhee et al. |
| 5,304,542 A | 4/1994 | Tatakis |
| 5,354,557 A | 10/1994 | Oppermann et al. |
| 5,461,034 A | 10/1995 | Rodan et al. |
| 5,470,831 A * | 11/1995 | Whitman et al. .............. 514/15 |
| 5,470,911 A | 11/1995 | Rhee et al. |
| 5,504,190 A | 4/1996 | Houghten et al. |
| 5,578,569 A | 11/1996 | Tam |
| 5,643,549 A * | 7/1997 | Rhodes ...................... 424/1.69 |
| 5,661,127 A | 8/1997 | Bhatnagar et al. |
| 5,776,892 A * | 7/1998 | Counts et al. ................. 514/11 |
| 5,786,327 A | 7/1998 | Tam |
| 5,792,664 A | 8/1998 | Chait et al. |
| 5,880,094 A | 3/1999 | Tam |
| 6,117,839 A | 9/2000 | Tam |
| 6,274,702 B1 | 8/2001 | Tam |
| 6,352,973 B1 | 3/2002 | Tam |

FOREIGN PATENT DOCUMENTS

| | | |
|---|---|---|
| EP | 0451867 | 10/1991 |
| EP | 0499242 | 8/1992 |
| EP | 0504938 | 9/1992 |
| GB | 2231872 | 7/1992 |
| WO | WO90/00060 | 1/1990 |
| WO | WO 90/06321 * | 6/1990 |
| WO | WO91/11515 | 8/1991 |
| WO | WO92/14481 | 9/1992 |
| WO | WO 94/05309 | 3/1994 |
| WO | WO 94/20615 | 9/1994 |
| WO | WO 95/28172 | 10/1995 |
| WO | WO 97/12036 | 4/1997 |

OTHER PUBLICATIONS

Dart et al. Transforming growth factors from a human tumor cell: characterization of transforming growth factor beta and identification of high molecular weight transforming growth factor alpha. Biochemistry, (Oct. 8, 1985) 24 (21) 5925–31.*
Bowie et al. Deciphering the message in protein sequences: tolerance to amino acid substitutions. Science. (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495.*
Ehlert et al. J Biol Chem. Mar. 17, 1995;270(11):6338–44, Oct. 1985.*
Alfred Walz and Marco Baggiolini: A Novel Cleavage Product of β–Thromboglobulin Formed in Cultures of Stimulated Mononuclear Cells Activates Human Neutrophils, vol. 159, No. 3, 1989; Mar. 31, 1989; pp. 969–975; Theodor–Kocher–Insitut, University of Bern, Switzerland.
Selye, "On the Stimulation of New Bone–Formation . . . " Endocrinology 16: 547–558 (1933).
Aitken et al. "Primary Hyperparathyroidism with Osteosclerosis . . . " Am. J. Med. 37:813–820 (Nov. 1964).
Kalu et al., "Parathyroid Hormone and Experimental . . . " Lancet 1363–1366 (Jun. 1970).

(List continued on next page.)

Primary Examiner—David S. Romeo
(74) Attorney, Agent, or Firm—John C. Hunt

(57) ABSTRACT

Polypeptides which increase or promote mammalian bone growth, related nucleotide sequences, antibodies, diagnostic kits and treatments. Subsequences of the polypeptide (SEQ ID NO:2)Asp Ser Asp Leu Tyr Ala Glu Leu Arg Cys Met Cys Ile Lys Thr Thr Ser Gly Ile His Pro Lys Asn Ile Gln Ser Leu Glu Val Ile Gly Lys Gly Thr His Cys Asn Gln Val Glu Val Ile Ala Thr Leu Lys Asp Gly Arg Lys Ile Cys Leu Asp Pro Asp Ala Pro Arg Ile Lys Lys Ile Val Gln Lys Lys Leu Ala Gly Asp Glu Ser Ala Asp have been shown to promote growth. Subsequences include (SEQ ID NO:11) Asp Ser Asp Leu Tyr Ala Glu Leu Arg Cys Met Cys Ile Lys Thr Thr Ser Gly Ile His Pro Lys Asn Ile Gln Ser (SEQ ID NO:12); Ile Lys Thr Thr Ser Gly Ile His Pro Lys Asn Ile Gln Ser (SEQ ID NO:13); Cys Met Cys Ile Lys Thr Thr Ser Gly Ile His Pro Lys Asn Ile Gln Ser and (SEQ ID NO:19) TTSGIHPK.

3 Claims, 5 Drawing Sheets

OTHER PUBLICATIONS

Klein et al., "Prostaglandins: Simulation of Bone Resorption . . . " Endocrinology 86: 1436–14 1440 (Jun. 1970).

Connor et al., "Generalized Osteosclerosis in Primary . . . " Trans Am. Clin. Climato. Assoc. 85: 185–201 (1973).

Genant, "Osteosclerosis in Primary Hyperparathyroidism" Am. J. Med. 59: 104–113 (Jul. 1975).

Rudinger et al. Peptide Hormones. Parsons, eds., University Park Press, Baltimore, pp. 1–7, 1976.

Tam et al.,"Bone Apposition Rate as an Index of . . . " Metabolism 27(2): 143–150 (Feb. 1978).

Begg et al., "Complete Covalent Structure of Human.beta–Thromboglobulin", Structure of .beta–Thromboglobulin, vol. 17, No. 9, 1978, pp. 1739–1744.

Schulz et al., Principles of Protein Structure, Springer–Verlag, New York, pp. 14–16, 1979.

Marks et al., "The Hematogenous Origin of Osteoclasts: Experimental . . . " Am. J. Anat 161:1–10 (1981).

Chen, "Glucocorticoid Regulation of 1.25(OH)2–Vitamin D3 . . . " J. Bio. Chem. 257(22):13564–13569 (Nov. 1982).

Parfitt, "The Coupling of Bone Formation to Bone . . . " Metab. Bone Dis & Rel. Res. 4:1–6 (1982).

Tam et al., "Parathyroid Hormone Stimulates the Bone . . . " Endocrinology 110(2):506–512 (1982).

C.W. Castor et al., "Structural and Biological Chacteristics of Connective Tissue Activating Peptide (CTAP–III), a Major Human Platelet–3 derived Growth Factor", Proc. Natl. Acad. Sci. USA, vol. 80, Fed. 1983, pp. 765–769.

Chyun, "Stimulation of Bone Formation by Prostaglandin E2" Prostaglandins J. 27(1):97–103 (Jan. 1984).

Canalis, "Effect of Growth Factors on Bone Cell . . . " Clin. Orthop. & Rel. Res. 246–263 (1985).

Dart et al. Transforming growth factors from a human tumor cell: characterization of transforming growth factor beta and identification of high molecular weight transforming growth factor alpha. Biochemistry, (Oct. 8, 1985) 24 (21) 5925–31.

Owen, "Lineage of Osteogenic Cells and Their . . . " Bone & Mineral Res. 3(1):1–25 (1985).

Sundelin et al., "The Primary Structure of Rabbit and Rat Prealbumin . . . " J. Biol. Chem. 260(10):6481–6487 (May 1985).

George et al., Macromolecular Sequencing and Synthesis: Selected Methods and Applications, Schlesinger, ed., Alan R. Liss Inc., New York, pp. 127–149, 1988.*

Castor et al., "Connective Tissue Activation–Biologically Active Cleavage Products of CTAP–III From Human Platelets", Biochemical and Biophysical Research Communications, vol. 163, No. 2, 1989, pp. 1071–1078.

Noda et al. In vivo stimulation of bone formation by transforming growth factor–beta.Endocrinology, (Jun. 1989) 124(6) 2991–4.

Tam, "The Pathogenesis of Metabolic Bone Disease . . . " CRC Press, Boca Raton 2: 19–31 (1989).

Bowie et al. Science 247: 1306–1310, 1990.

Walz et al., "Generation of the Neutrophil–Activating Peptide NAP–2 from Platelet Basic Protein or Connective Issue–3 Activating Peptide III Through Monocyte Proteases", Journal of Med., vol. 171, Feb. 1990, pp. 449–454.

Wells, Biochemistry 29:8509–8517, 1990.*

Wozney et al., J. Cell. Sci. Suppl. 13:149–156 (1990).

Castor et al., "Connective Tissue Activation", Arthritis & Rheumatism, vol. 35, No. 7, Jul. 1992, pp. 783–793.

Roodman, "Perspectives: Interleukin–6: An Osteotropic Factor?" J. Bone & Mineral Res. 7(5):475–478 (1992).

Ngo et al. The Protein Folding Problem and Tertiary Structure Prediction. Merz et al, eds., Birkhauser, Boston, pp. 491–495, 1994.

Vaughan et al., Identification and Characterization of the Insertion Element IS1070 from *Leuconostoc lactis* NZ6009, Elsevier Science B.V. pp. 95–100 (1995).

Navab et al., "Rat Plasma Prealbumin" J. Biol. Chem. 252:5100–5106 (Jul. 1997).

Vaughan et al., U17353, *Leuconostoc lactis* insertium sequence IS1070:Is1070 putative transposase (tnp) gene, complete eds. Sep. 13, 1995.

Stedman's Medical Dictionary, 27$^{th}$ edition Medical Economics Company, Inc. 2000.

Abstract—WO 92/10515, PHARMA Bissendorf Peptide GMBH, Derivatives of the Human Parathormone Fragment (1–37) in the Amide or Ethylamide Form as Active Substance, Jun. 25, 1992.

Abstact—WO 92/15615, Chugai Seiyaku Kabushiki Kaisha, Serum Calcium Depressing Factor, Sep. 17, 1992.

Coccia et al. "Successful Bone–Marrow Transplantation . . . " New England Journal of Medicine 302(13) 701–708 (1980).

Canalis, "Interleukin–1 has Independ Effects on Deoxribonucleic . . . " Endocrinology 118(1):74–81 (1986).

Centrella et al., "Transforming and Non–Transforming Growth Factors are . . . " Proc. Natl. Acad. Sci USA 82:7335–7339 (Nov. 1985).

Canalis, "Effect of Insulin–like Growth Factor I on DNA . . . " J. Clin. Invest. 66:709–719 (Oct. 1980).

Tashjian et al. "α and β Human Transforming Growth Factors . . . " Proc. Natl. Acad. Sci. USA 82:4535–4538 (Jul., 1985).

Majumdar et al. "Characterization of the Human β–thromboglobulin . . . " J. Bio. Chem 266(9):5785–5787 (Mar. 1991).

Ehlert, et al. "Limited and defined truncation at the C terminus enhances receptor binding and degranulation activity of the neutrophil–activating peptide 2 (NAP–2)," Journal of Biological Chemistry, vol. 270, No. 11, 6338–6344 (1995).

International Search Report issued by European Patent Office on international patent application No. PCT/CA96/00653, published Jun. 5, 1997.

International Search Report issued by European Patent Office on international patent application No. PCT/CA00/00031, published Jul. 20, 2000.

Schumacher et al., "High–and Low–Affinity binding of GROα and Neutrophil–Activating peptide 2 to Interleukin 8 receptors on Human Neutrophils," Proc. Natl. Acad. Sci. USA, 89:10542–10546, (Nov. 1992).

International Search Report issued by European Patent Office on International patent application No. PCT/CA95/00205, published Oct. 26, 1995.

* cited by examiner

Active Sequences:

SEQ ID NO:1      AELRCMCIKTTSGIHPKNIQSLEVIGKGTHCNQVEVIATLKDGRKICLDPDAPRIKKIVQKKLAGDESAD
(MW=7670)        6    10    15    20    25    30    35    40    45    50    55    60    65    70

SEQ ID NO:2      DSDLYAELRCMCIKTTSGIHPKNIQSLEVIGKGTHCNQVEVIATLKDGRKICLDPDAPRIKKIVQKKLAGDESAD
(MW=8218)

SEQ ID NO:11     DSDLYAELRCMCIKTTSGIHPKNIQS
(MW=2850)

SEQ ID NO:12     IKTTSGIHPKNIES
(MW=1530)

SEQ ID NO:13     CMCIKTTSGIHPKNIQS
(MW=1862)

Inactive Sequences:

SEQ ID NO:14     MCIKTTSGIHPKNIQS
(MW=1750)

SEQ ID NO:15     CIKTTSGIHPKNIQS
(MW=1643)

FIGURE 5

BONE STIMULATING FACTOR

This application is a continuation-in-part of U.S. application Ser. No. 09/048,058 filed Mar. 26, 1998, now abandoned, incorporated herein by reference, which is a continuation of International Application No. PCT/CA 96/00653 filed Sep. 26, 1996, now abandoned, incorporated herein by reference, and which claims the benefit of U.S. Provisional Application No. 60/004,314, filed Sep. 26, 1995, now expired, incorporated herein by reference.

The present invention relates to polypeptides which stimulate bone growth.

Understanding of issues related to bone growth and strength has progressed over the years, a summary being provided in, for example, international patent application No. PCT/CA 94/00144, published on Sep. 15, 1994 under WO 94/20615, U.S. Pat. No. 5,320,970 and European patent application No. 92 302 446, published under 505 210 on Sep. 23, 1992, the contents of which applications are incorporated herein by reference.

By way of background to the present invention, described below, neutrophil-activating peptide (NAP-2; SEQ ID NO:1) and a variant of NAP-2, here termed "NAP-2V" (SEQ ID NO:2) have been known for some time (Walz, A., and M. Baggiolini, (1989) *Biochem. Biophys. Res. Commun.* 159:969). British Patent No.2 231 872 (British Patent No. 2 231 872. Inventors: M. Baggiolini, K. J. Clemetson, and A. Walz. Published Jun. 14, 1990.), describes the amino acid sequence of NAP-2 and three apparently naturally occurring variants, including NAP-2V. The other two variants have an additional four (SEQ ID NO:3) and three (SEQ ID NO:4) amino acids at the N-terminal of the NAP-2 sequence. NAP-2 is a subsequence of β-thromboglobulin (β-TG; SEQ ID NO:5) which has an additional eleven amino acids at the N-terminal end. β-TG is itself a subsequence of connective tissue-activating peptide (CTAP-III; SEQ ID NO:6) which has an additional four amino acids at the N-terminal. CTAP-III is a subsequence of platelet basic protein (PBP; SEQ ID NO:7) which has an additional nine amino acids at the N-terminal.

NAP-2 along with interleukin-8 (human IL-8; SEQ ID NO:8; porcine IL-8 SEQ ID NO:9) and melanoma growth-stimulating activity (MGSA) have been assigned to a subfamily known as the α-chemokines. The α-chemokines have in common with each other four cysteine residues at highly conserved positions, which enclose the core region of the molecules, as described by Brandt et al (Ehlert, J. E., F. Peterson, M. H. G. Kubbuta, J. Gerdes, H.-D. Flad, and E. Brandt, (1995) *J. Biol. Chem.* 270:6338). Brandt et al. found an apparently naturally occurring C-terminus truncated variant of NAP-2, lacking the last four amino acids of NAP-2, that displays enhanced increase in potency to stimulate neutrophil degranulation. Brandt et al. also synthesized variants lacking the final one, two, three, five and six amino acids of the C-terminus of NAP-2. All of these C-truncated polypeptides exhibited a moderate increase in potency over NAP-2 with the exception of the sequence having only the first sixty-four amino acids of NAP-2. Brandt et al. discussed the possible significance of the sequence modifications with respect to the structure of NAP-2 and its function.

Platelet factor 4 (PF4; SEQ ID NO:10) is a seventy amino acid polypeptide (Hermodson, M., G. Schmer and K. Kurachi, (1977) *J. Biol. Chem.* 252:6276; Morgan, F. J., G. S. Begg, C. N. Chesterman, (1979) *Thromb. Haemost* 42:1652). PF4 has been shown to inhibit proliferation of two osteoblastic osteosarcoma cell lines, Saos-2 and G-292 (U.S. Pat. No. 5,304,542. Inventor: D. M. Tatakis. Issued Apr. 19, 1994). Indomethacin apparently did not affect PF4-induced inhibition of the cell proliferation. Particular fragments, PF4(58-70), PF4(47-70) and monomeric low-affinity PF4 (LAPF4), which is 50% homologous to PF4 and contains an α-helical C-terminus were also suggested as being useful. PF4 and such related polypeptides were thus described as being useful in a method for inhibiting proliferation of osteoblasts, in among other things, humans suffering from osteoporosis.

The first 70 amino acids of NAP-2V and the sequence of PF4 are about 51% homologous and the positions of the four cysteine residues are conserved between the two polypeptides.

It has now been shown that NAP-2, NAP-2V, as well as subsequences of NAP-2V also show bone stimulatory effects, while certain subsequences do not display bone stimulatory activity. NAP-2V-(1-26) (SEQ ID NO:11) and NAP-2V-(13-26; gln$^{25}$→glu$^{25}$) (SEQ ID NO:12) were found to increase the observed bone apposition rate, the latter of the two being more potent than the former. NAP-2V-(10-26) (SEQ ID NO:13) appeared to cause a small increase in the observed bone apposition rate, although the statistical significance of the observed increase was questionable. Protected versions of NAP-2V-(13-26; gln$^{25}$→glu$^{25}$) (SEQ ID NO:17) and of NAP-2V-(15-22) (SEQ ID NO:18) were also found to have bond stimulatory activity. NAP-2V-(11-26) (SEQ ID NO:14) and NAP-2V-(12-26) (SEQ ID NO:15) were found to have no effect on observed bone mineral apposition rate.

The invention thus includes a compound which promotes bone growth in mammals, comprising an amino acid sequence which consists essentially of:
  (i) up to 69 consecutive amino acids of the sequence corresponding to SEQ ID NO:2 with (a) from 6 to about 14 amino acids deleted from the N-terminus of SEQ ID NO:2, or (b) 7 to about 53 amino acids deleted from the C-terminus of SEQ ID NO:2, or both (a) and (b) and wherein the sequence includes no cysteine residues or at least two cysteine residues;
  (ii) a variant of a polypeptide of (i) containing a plurality of said amino acid sequences;
  (iii) a conservatively substituted variant of a polypeptide of (i) or (ii); or
  (iv) a functionally equivalent homologue of (i), (ii) or (iii).

In another aspect, the invention includes a polypeptide in which the amino acid sequence consists essentially of an amino acid sequence corresponding to SEQ ID NO:11, or corresponding to SEQ ID NO:11 with from 6 to about 14 amino acids deleted from the N-terminus of SEQ ID NO:11, or corresponding to SEQ ID NO:11 with from 6 to about 12 amino acids deleted from the N-terminus of SEQ ID NO:11; or corresponding to SEQ ID NO:11 with from 6 to about 9 amino acids deleted from the N-terminus of SEQ ID NO:11; or a functionally equivalent homologue any of the foregoing polypeptides.

A polypeptide of the present invention can have an amino acid sequence which consists essentially of an amino acid sequence corresponding to SEQ ID NO:12, or SEQ ID NO:13, or SEQ ID NO:18, or a functionally equivalent homologue of any of these.

The present invention includes a compound "derived from" any of the preceding polypeptides.

The present invention thus includes a polypeptide wherein the amino acid sequence consists essentially of:
  (v) an amino acid sequence corresponding to SEQ ID NO:12;

(vi) an amino acid sequence corresponding to SEQ ID NO:13;

(vii) an amino acid sequence corresponding to SEQ ID NO:18;

(viii) a variant of a polypeptide of (v), (vi) or (vii) containing a plurality of said amino acid sequences; or (ix) a conservatively substituted variant of a polypeptide of (v), (vi), (vii) or (viii).

In preferred embodiments, a polypeptide of the present invention that cysteine residues, includes two cysteine residues that are located at positions corresponding to the tenth and twelfth positions of SEQ ID NO:2.

A polypeptide of the present invention can have, if desired, or necessary, one or the other or both of the N-terminal amino acid and the C-terminal amino acid protected by a protecting group.

The polypeptide can be synthetic and the amino acid sequence can have a molecular weight in the range of from about 1000 to 4000 daltons; or from about 1000 to about 3000; or from about 1000 to about 2000; or more preferably from about 1200 to about 1800.

In another aspect, the invention is a first polypeptide which promotes bone growth in mammals comprising a sequence of amino acids which consists essentially of up to 69 amino acids and is sufficiently duplicative of a second polypeptide such that the first polypeptide is encoded by a DNA that selectively hybridizes under stringent conditions with DNA encoding the second polypeptide. In this instance, the second polypeptide comprises an amino acid sequence which consists essentially of:

(i) up to 69 consecutive amino acids of the sequence corresponding to SEQ ID NO:2 with (a) from 6 to about 14 amino acids deleted from the N-terminus of SEQ ID NO:2, or (b) 7 to about 53 amino acids deleted from the C-terminus of SEQ ID NO:2, or both (a) and (b) and wherein the sequence includes no cysteine residues or at least two cysteine residues;

(ii) a variant of a polypeptide of (i) containing a plurality of said amino acid sequences;

(iii) a conservatively substituted variant of a polypeptide of (i) or (ii); or (iv) a functionally equivalent homologue of (i), (ii) or (iii).

The DNA sequence of NAP-2V disclosed by Walz et al. (British Patent No. 2 231 872. Inventors: M. Baggiolini, K. J. Clemetson, and A. Walz. Published Jun. 14, 1990. Neutrophil-activating peptide-2 and processes for the production of NAP-2, B-TG, CTAP-III and PBP) is identified here as SEQ ID NO:16.

The phrase "selectively hybridizes to" refers to a nucleic acid molecules that, under appropriately stringent hybridization conditions, hybridize, duplex or bind essentially only to each other when molecules having the predefined sequences (i.e., second polypeptide) are present in a preparation of DNA or RNA. For discussions of nucleic acid molecule design and annealing conditions, see, for example, Sambrook et al., Molecular Cloning: A Laboratory Manual (2nd ed.), Vols. 1–3, Cold Spring Harbor Laboratory, (1989) or Current Protocols in Molecular Biology, F. Ausubel et al., (ed.) Greene Publishing and Wiley-Interscience, New York (1987).

It will, of course, be understood by those skilled in the art that portions of the nucleic acid sequence identified as SEQ ID NO:16 correspond to sequences coding for the polypeptides identified as SEQ ID NO:1, NO:11; NO:12 (Glu→Gln) or NO:13. For example, nucleic acids 37 through 78 of SEQ ID NO:16 encode the amino acid subsequence identified as SEQ ID NO:12 in which the penultimate amino acid of the subsequence is glutamine.

"Stringent hybridization conditions" takes on its common meaning to a person skilled in the art here. Appropriate stringency conditions which promote nucleic acid hybridization, for example, 6×sodium chloride/sodium citrate (SSC) at about 45° C. are known to those skilled in the art. The following examples are found in Current Protocols in Molecular Biology, John Wiley & Sons, NY (1989), 6.3.1–6.3.6: For 50 ml of a first suitable hybridization solution, mix together 24 ml formamide, 12 ml 20×SSC, 0.5 ml 2 M Tris-HCl pH 7.6, 0.5 ml 100×Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2×SSC at 50° C. to a high stringency of about 0.2×SSC at 50° C. Both of these wash solutions may contain 0.1% SDS. In addition, the temperature in the wash step can be increased from low stringency conditions at room temperature, about 22° C. to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3–5° C. intervals until background is low enough not to be a major factor in autoradiography.

Alternatively, such a first polypeptide is a sequence of amino acids sufficiently duplicative of a second polypeptide having an amino acid sequence corresponding to SEQ ID NO:11 up to 69 amino acids in length, or corresponding to SEQ ID NO:11 with from 6 to about 12 amino acids deleted from the N-terminus of SEQ ID NO:11, or corresponding to SEQ ID NO:11 with from 6 to about 9 amino acids deleted from the N-terminus of SEQ ID NO:11; wherein the sequence includes no cysteine residues or at least two cysteine residues; or a functionally equivalent homologue, such that the first polypeptide is encoded by a DNA that hybridizes under stringent conditions with DNA encoding the second polypeptide. The second polypeptide can have, alternatively, or additionally 7 to about 53 amino acids deleted from the C-terminus of SEQ ID NO:2.

The first polypeptide can have a sequence of amino acids sufficiently duplicative of a second polypeptide having an amino acid sequence corresponding to SEQ ID NO:12 up to 69 amino acids in length; or a functionally equivalent homologue, such that the first polypeptide is encoded by a DNA that hybridizes under stringent conditions with DNA encoding the second polypeptide.

The first polypeptide can have a sequence of amino acids sufficiently duplicative of a second polypeptide having an amino acid sequence corresponding to SEQ ID NO:11; or a conservatively substituted variant thereof, such that the first polypeptide is encoded by a DNA that hybridizes under stringent conditions with DNA encoding the second polypeptide; or it can have a sequence of amino acids sufficiently duplicative of a second polypeptide comprising an amino acid sequence corresponding to SEQ ID NO:12; or a conservatively substituted variant thereof, such that the first polypeptide is encoded by a DNA that hybridizes under stringent conditions with DNA encoding the second polypeptide; or it can have a sequence of amino acids sufficiently duplicative of a second polypeptide having an amino acid sequence corresponding to SEQ ID NO:13; or a conservatively substituted variant thereof, such that the first polypeptide is encoded by a DNA that hybridizes under stringent conditions with DNA encoding the second polypeptide; or it can have a sequence of amino acids sufficiently duplicative of a second polypeptide having an amino acid sequence corresponding to SEQ ID NO:18; or a conservatively substituted variant thereof, such that the first polypeptide is encoded by a DNA that hybridizes under stringent conditions with DNA encoding the second polypeptide.

A bone growth polypeptide of the invention can be of any suitable length, and particularly can be up to 8 amino acids in length, or up to 14 amino acids in length, or up to 20 amino acids in length, or up to 30 amino acids in length, or up to 40 amino acids in length, or up to 50 amino acids in length, or up to 60 amino acids or more in length.

The invention includes any number of chimeric bone stimulating factors made having an amino acid sequence of polypeptides of the present invention.

In another aspect, the invention is an agent for use in prevention and treatment of a bone reduction related disease which includes any polypeptide or polypeptides of the present invention as an active ingredient.

The invention is, alternatively, a pharmaceutical composition for promoting bone growth, having a therapeutically effective amount of a polypeptide or polypeptides of the present invention.

The invention includes a method of increasing bone growth in a mammal by administering a therapeutically effective amount of a polypeptide having an amino acid sequence of a polypeptide or polypeptides of the present invention.

The invention includes use of a polypeptide or polypeptides of the present invention for the treatment of osteoporosis. Alternatively, the use of a polypeptide or polypeptides can be to promote bone growth in a mammal.

The invention includes use of the polypeptide or polypeptides in the preparation of a medicament for use in promoting bone growth or the treatment of osteoporosis.

The invention includes a diagnostic kit for determining the presence of a polypeptide or polypeptides of the present invention. The kit can includes an antibody to a said polypeptide(s) linked to a reporter system wherein the reporter system produces a detectable response when a predetermined amount of the polypeptide(s) and the antibody are bound together.

The invention includes an antibody synthesized using a polypeptide consisting of an amino acid sequence identified as SEQ ID NO:11; SEQ ID NO:12; or SEQ ID NO:13 or a conservatively substituted variant thereof.

More generally, the invention includes an antibody which binds to a polypeptide or polypeptides of the present invention, synthesized using the polypeptide(s).

The invention includes an isolated DNA fragment which encodes the expression of any of the polypeptides of the present invention, and DNA which differs from the fragment due to the degeneracy of the genetic code.

The invention includes a vector comprising a DNA sequence which encodes the expression of any of any of the polypeptides of the present invention.

The invention includes a process for producing a polypeptide of the invention which includes the steps of:

a) preparing a DNA fragment containing a nucleotide sequence which encodes the polypeptide;

b) incorporating said DNA fragment into an expression vector to obtain a recombinant DNA fragment which contains the DNA fragment and is capable of undergoing replication;

c) transforming a host cell with the recombinant DNA fragment to isolate a transformant which can express the polypeptide; and d) culturing the transformant to allow the transformant to produce the polypeptide and recovering the polypeptide from resulting cultured mixture.

In yet another aspect, the invention is a synthetic polypeptide up to 65 amino acids in length, having in vivo bone stimulatory activity in mammals, having an amino acid sequence which is at least about 11% conserved in relation to the amino acid sequence identified as SEQ ID NO:2 (i.e., contains 8 consecutive amino acids of the sequence identified as SEQ ID NO:2); a conservatively substituted variant thereof; or a functionally equivalent homologue.

The synthetic polypeptide can also be at least about 11%, 12%, 13%, 15%, 16%, 17%, 19%, 22%, 25%, 28%, 31%, or 35% conserved in relation to the amino acid sequence identified as SEQ ID NO:2; a conservatively substituted variant thereof; or a functionally equivalent homologue.

Such a synthetic polypeptide can have at least 49 amino acids deleted from the sequence.

The polypeptide can have no cysteine residues or at least two cysteine residues.

The polypeptide can have a molecular weight in the range of from about 1000 to 4000.

In another aspect, the present invention is a first polypeptide having a sequence of amino acids sufficiently duplicative of a second polypeptide which includes an amino acid sequence of any of the synthetic polypeptides, such that the first polypeptide is encoded by a DNA that hybridizes under stringent conditions with DNA encoding the second polypeptide.

The invention includes a chimeric bone stimulating factor comprising an amino acid sequence of any of the synthetic polypeptides.

An agent of the present invention for use in prevention and treatment of a bone reduction related disease can include one or more of the synthetic polypeptides.

As well, a pharmaceutical composition of the present invention for promoting bone growth, can include a therapeutically effective amount of a one or more of the synthetic polypeptides.

The invention includes a method of increasing bone growth in a mammal by administering a therapeutically effective amount of one or more of the synthetic polypeptides.

Such a synthetic polypeptide can be used for the treatment of osteoporosis or to promote bone growth in a mammal.

Such a synthetic polypeptide can be used in the preparation of a medicament for use in promoting bone growth or the treatment of osteoporosis.

The invention includes a diagnostic kit for determining the presence of one or more the synthetic polypeptides, the kit including antibody(ies) to a the polypeptide(s) linked to a reporter system wherein the reporter system produces a detectable response when a predetermined amount of the polypeptide(s) and the antibody(ies) are bound together.

The invention includes an antibody which binds to one or more of the synthetic polypeptides, synthesized using the polypeptide.

Further still, the invention includes an isolated DNA fragment which encodes the expression of any of the synthetic polypeptides, and DNA which differs from the fragment due to the degeneracy of the genetic code. The invention includes a vector which includes such a DNA sequence.

The invention includes a process for producing any of the synthetic polypeptides, which includes:

a) preparing a DNA fragment containing a nucleotide sequence which encodes a polypeptide;

b) incorporating said DNA fragment into an expression vector to obtain a recombinant DNA fragment which contains the DNA fragment and is capable of undergoing replication;

c) transforming a host cell with the recombinant DNA fragment to isolate a transformant which can express the polypeptide; and d) culturing the transformant to allow the transformant to produce the polypeptide and recovering the polypeptide from resulting cultured mixture.

The invention includes a polypeptide exhibiting bone stimulatory activity in mammals, the polypeptide being up to 65 amino acids in length and having the sequence identified as SEQ ID NO:11, SEQ ID NO:12, or SEQ ID NO:13; analogues thereof wherein the amino acids in the sequence may be substituted, deleted or added, so long as the bone stimulatory activity in mammals derived the three dimensional structure of the sequence is preserved; and conjugates of each of the polypeptides or analogues thereof, wherein if the polypeptide sequence contains a cysteine residue, there are at least two cysteine residues. Such a polypeptide can be substantially pure and the amino acid sequence can have a molecular weight in the range of from about 1000 to about 4000, or from about 1500 to about 3000, or from about 1500 to about 1800. The invention is also a first polypeptide that includes a sequence of amino acids sufficiently duplicative of a second polypeptide having an amino acid sequence corresponding such a polypeptide, or a functionally equivalent homologue thereof, such that the first polypeptide is encoded by a DNA that hybridizes under stringent conditions with DNA encoding the second polypeptide; or a chimeric bone stimulating factor including such an amino acid sequence; or an agent for use in prevention and treatment of a bone reduction related disease which includes such a polypeptide as an active ingredient; or a pharmaceutical composition for promoting bone growth, having a therapeutically effective amount of such a polypeptide; or a method of increasing bone growth in a mammal by administering a therapeutically effective amount of such a polypeptide; having an amino acid sequence of a polypeptide defined in claim 56 or 57; or the use of such a polypeptide for the treatment of osteoporosis or to promote bone growth in a mammal; or the use of such a polypeptide in the preparation of a medicament for use in promoting bone growth or the treatment of osteoporosis; or a diagnostic kit for determining the presence of such a polypeptide, the kit including an antibody to a the polypeptide linked to a reporter system wherein the reporter system produces a detectable response when a predetermined amount of the polypeptide and the antibody are bound together; or an antibody which binds to such a polypeptide, synthesized using the polypeptide; or an isolated DNA fragment which encodes the expression of any such polypeptide, or which differs from the fragment due to the degeneracy of the genetic code; or a vector including a DNA sequence which encodes the expression of any such polypeptide; or a process for producing such a polypeptide, which process includes:

a) preparing a DNA fragment containing a nucleotide sequence which encodes the polypeptide;

b) incorporating the DNA fragment into an expression vector to obtain a recombinant DNA fragment which contains the DNA fragment and is capable of undergoing replication;

c) transforming a host cell with the recombinant DNA fragment to isolate a transformant which can express the polypeptide; and d) culturing the transformant to allow the transformant to produce the polypeptide and recovering the polypeptide from resulting cultured mixture.

Finally, the invention includes an isolated DNA sequence encoding the amino acid sequence of any of the polypeptides of the invention, or an analogue thereof, wherein the amino acids in the sequence may be substituted, deleted or added, so long as bone stimulatory activity in mammals derived from the three dimensional conformation of the sequence is preserved in a polypeptide comprising the amino acid sequence; sequences which hybridize to the DNA and encode an amino acid sequence of a polypeptide which displays bone stimulatory activity in mammals; and DNA which differs from the sequence due to the degeneracy of the genetic code.

DESCRIPTION OF THE DRAWINGS

FIG. 5 illustrates the amino acid sequences of polypeptides tested, corresponding amino acids aligned with each other, the active peptides being shown above the line and sequences which were not found to stimulate bone growth being below the line. Approximate molecular weights are shown below the sequence identification numbers.

MATERIALS, METHODS AND RESULTS

Polypeptides having the sequences of NAP-2 (SEQ ID NO:1) and NAP-2V (SEQ ID NO:2) were chemically synthesized directly according to standard methods and experiments were conducted to determine whether the chemically synthesized polypeptides displayed activity.

Experiments were conducted simultaneously on three groups of male Sprague-Dawley rats, there being five rats in each group. Each rat weighed between 250 and 350 g. Each rat of the first group was given, by subcutaneous injection into the left gluteus maximus region, 200 $\mu$l of a 1% aqueous acetic acid solution containing 25 nmol (about 191 $\mu$g) of NAP-2 (SEQ ID NO:1). Each rat of the second group was similarly given 200 µl of a 1% aqueous acetic acid solution containing 25 nmol (about 207 µg) of NAP-2V (SEQ ID NO:2). Each rat of the third group, the control group, was similarly given 200 µl of 1% acetic acid solution.

Immediately following administration of the test solution, 300 µl of an aqueous solution of tetracycline hydrochloride was administered intramuscularly into the right gluteus maximus, the concentration of tetracycline being sufficient to obtain a dosage of about 24 mg/kg of rat body weight. A second dose of tetracycline hydrochloride solution was administered about 48 hours after the first dose. The rats were sacrificed about 24 hours after administration of the second dose of tetracycline.

Sections of the lower metaphysis of the right femur were used for bone measuring the bone mineral apposition rate. Processing of the bone material for measurement has been described previously. See, for example, international patent application No. PCT/CA 94/00144 published under No. WO 94/20615 on Sep. 15, 1994. The results obtained are summarized in Table One and FIG. 1.

TABLE ONE

Figure 1:
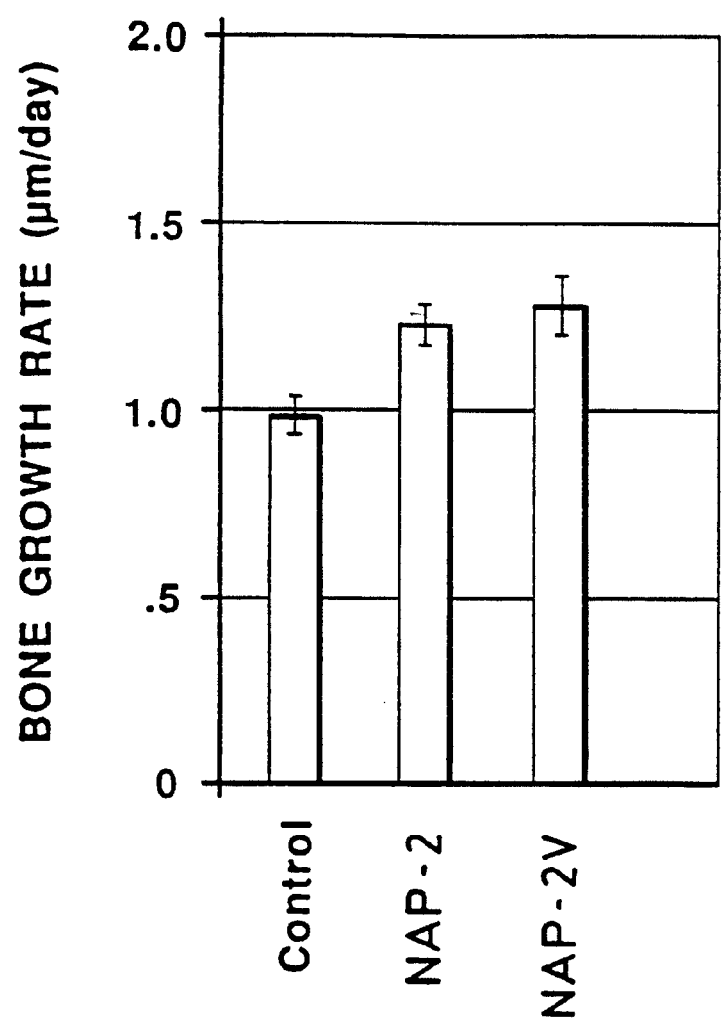
FIG. 1 shows the bone apposition rate ($\mu$m per day) for rats injected with 25 nmol (N=5 in both cases) of chemically synthesized polypeptides having the sequences of NAP-2 (SEQ ID NO:1) and NAP-2V (SEQ ID NO:2), respectively, compared to that of a group of control (N=5) rats. The error bars are ±1 S.D.

Comparison of the Group Arithmetic Means of Bone Apposition Rates (µm/day) Among Groups Administered with NAP-2, NAP-2V and control solutions shown in FIG. 1

|  | Control | SEQ ID NO: 1 | SEQ ID NO: 2 |
|---|---|---|---|
| Mean | 0.99 µm/d | 1.23 µm/d | 1.28 µm/d |
| S.D. | 0.04 | 0.05 | 0.08 |
| N | 5 | 5 | 5 |

|  | t | d.f. | p |
|---|---|---|---|
| Control Group vs SEQ ID NO: 1 | 7.91 | 8 | <0.001 |
| Control Group vs SEQ ID NO: 2 | 7.03 | 8 | <0.001 |
| SEQ ID NO: 1 vs SEQ ID NO: 2 | 1.15 | 8 | >0.20 |

Polypeptides having the sequence corresponding to either SEQ ID NO:1 or SEQ ID NO:2 have thus been found to stimulate bone growth.

In a second set of experiments, twenty-four male Sprague-Dawley rats (Charles River Laboratory) were divided into six groups of four. Each of the first group, the control group, was injected in the right thigh with 200 µl of 0.1% acetic acid solution. The rats of the other groups were each injected in the right thigh with about 200 µl of a 0.1% acetic acid solution containing about 25 nmol of a chemically synthesized polypeptide as follows:

| Group | Polypeptide | SEQ ID NO |
|---|---|---|
| A | NAP-2V-(1–26) | 11 |
| B | NAP-2V-(13–26; gln$^{25}$→ glu$^{25}$) | 12 |
| C | NAP-2V-(10–26) | 13 |
| D | NAP-2V-(11–26) | 14 |
| E | NAP-2V-(12–26) | 15 |

Immediately after injection of the polypeptide (control) solution, each rat was injected in the right gluteus maximus with 200 µl of a 1 M tetracycline hydrochloride (Sigma Chemical) solution. This dosage of tetracycline is about 16 mg per kg of animal body weight.

About 48 hours later, each rat was injected in the left gluteus maximus with the same dosage of tetracycline. Twenty-four hours later, the rats were sacrificed by $CO_2$ narcosis and the right femur taken for bone mineral apposition rate determination. One rat died during the course of the experiments.

Immediately after dissection, a bone sample was fixed in 10% formaldehyde solution at pH 7.4. Later the same day, a 1:1 $H_2O$-acetone solution was exchanged for the formaldehyde solution. This was exchanged twice the following day with acetone. This was exchanged the following day by a 1:1 acetone-Spurr's medium solution, which was exchanged later the same day with Spurr's medium. The following day each sample was embedded in a fresh change of Spurr's medium and cured at 60° C. for 24 hours, followed by curing at 80° C. for 24 hours.

Each cured block was cut into 400 µm thick sections using a Leitz saw microtome equipped with a diamond charged blade. The relatively thick sections were ground down between two ground glass plates pre-roughened with carborundum powder to a final thickness of about 10 µm, water being used as the grinding lubricant. The thin sections were dried and mounted unstained in Permount (Fisher).

Measurements were made using a Leitz scanning light microscope photometer MPV-CD magnifying the sections 16×, as described in international patent application No. PCT/CA94/00144.

Figure 2:
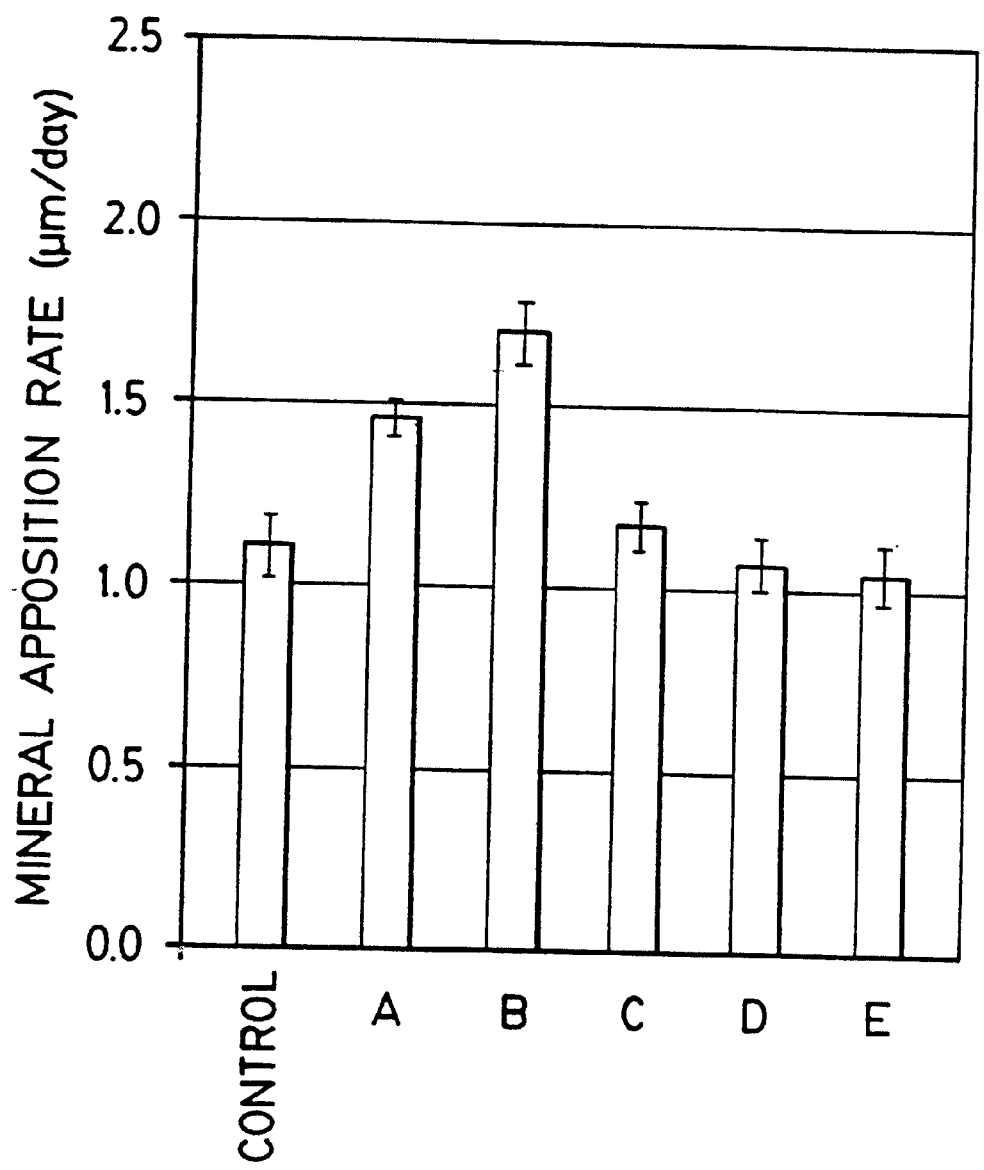
FIG. 2 graphically illustrates the observed bone mineral apposition rate ($\mu$m per day) for rats injected with chemically synthesized polypeptides of A, NAP-2V-(1-26) (SEQ ID NO:11); B, NAP-2V-(13-26; gln$^{25}$→glu$^{25}$) (SEQ ID NO:12,), C, NAP-2V-(10-26) (SEQ ID NO:13), D, NAP-2V-(11-26) (SEQ ID NO:14), and E, NAP-2V-(12-26) (SEQ ID NO:15). The first bar in the graph represents the control. The number of rats used for the determinations were 4, 4,3,4,4, and 4, respectively. The error bars are ±1 S.D.

The results obtained are shown in Table Two and FIG. 2.

TABLE TWO

Comparison of Group Arithmetic Means of Bone Apposition Rates (µm per day) shown in FIG. 2.

|  | Control | Group A | Group B | Group C | Group D | Group E |
|---|---|---|---|---|---|---|
| Mean | 1.08 | 1.47 | 1.70 | 1.18 | 1.07 | 1.04 |
| S.D. | 0.08 | 0.05 | 0.09 | 0.08 | 0.07 | 0.08 |
| N | 4 | 4 | 3 | 4 | 4 | 4 |

|  | t | d.f. | P |
|---|---|---|---|
| Control vs Group A | 7.90 | 6 | <0.001 |
| Control vs Group B | 9.69 | 5 | <0.001 |
| Group A vs Group B | 4.87 | 5 |  |

The polypeptide having the sequence identified as SEQ ID NO:12 has two sites susceptible to cleavage by the peptidase plasmin, between the lysine-threonine and the lysine-asparagine residues, respectively. In a third set of experiments, nine female Sprague-Dawley rats (average weight, about 300 gm) were divided into three groups of three. Each of the first group, the control group, was injected with 400 µl of buffer solution, 50 mM sodium acetate adjusted to pH 4.5 followed immediately by 200 µl of a 1M tetracycline hydrochloride solution. The rats of the second group were each injected with 400 µl of buffer containing 100 nmoles of a chemically synthesized polypeptide having the sequence identified as SEQ ID NO:17 followed immediately by 200 µl of a 1 M tetracycline hydrochloride solution. The rats of the third group were each injected with 400 µl of buffer containing 100 nmoles of a chemically synthesized polypeptide having the sequence identified as SEQ ID NO:18 followed immediately by 200 µl of a 1M tetracycline hydrochloride solution.

After about 48 hours, a second dose of tetracycline hydrochloride was administered to each rat. After about another 24 hours, rats were sacrificed by carbon dioxide narcosis.

The right femur of each animal was taken and treated, as described above, and measurements made as described above. The results obtained are shown in Table Three and FIG. 3.

TABLE THREE

Figure 3:
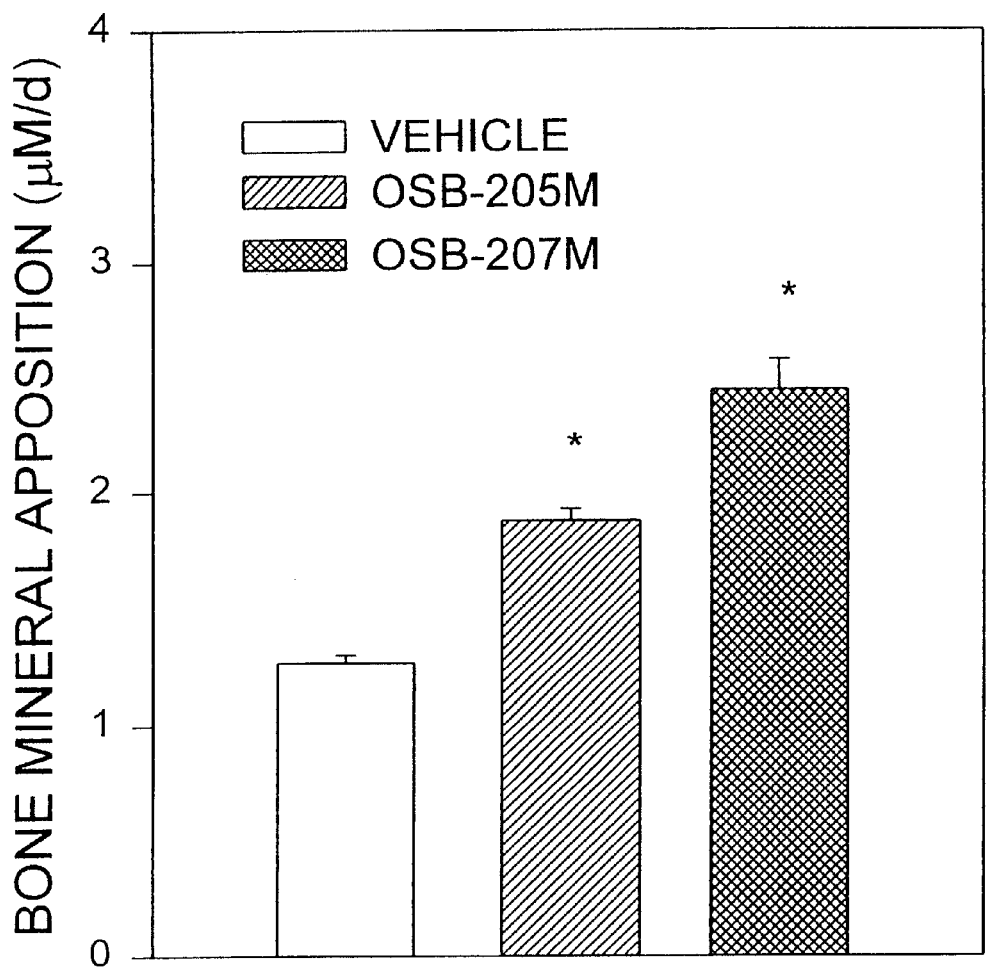
FIG. 3 graphically illustrates the observed bone mineral apposition rate ($\mu$m per day) for rats injected with chemically synthesized polypeptides having SEQ ID NO:17 (second bar), SEQ ID NO:18 (third bar) compared to a control (first bar). The error bars are ±1 S.E.

Comparison of the Group Arithmetic Means of Bone Apposition Rates (μm/day) Among Groups Administered with polypeptides having SEQ ID NO: 17, SEQ ID NO: 18, control solutions shown in FIG. 3

|  | Control | SEQ ID NO: 17 | SEQ ID NO: 18 |
|---|---|---|---|
| Mean | 1.256 μm/d | 1.859 μm/d | 2.406 μm/d |
| S.E. | 0.06 | 0.10 | 0.25 |
| N | 3 | 3 | 3 |

Figure 4:
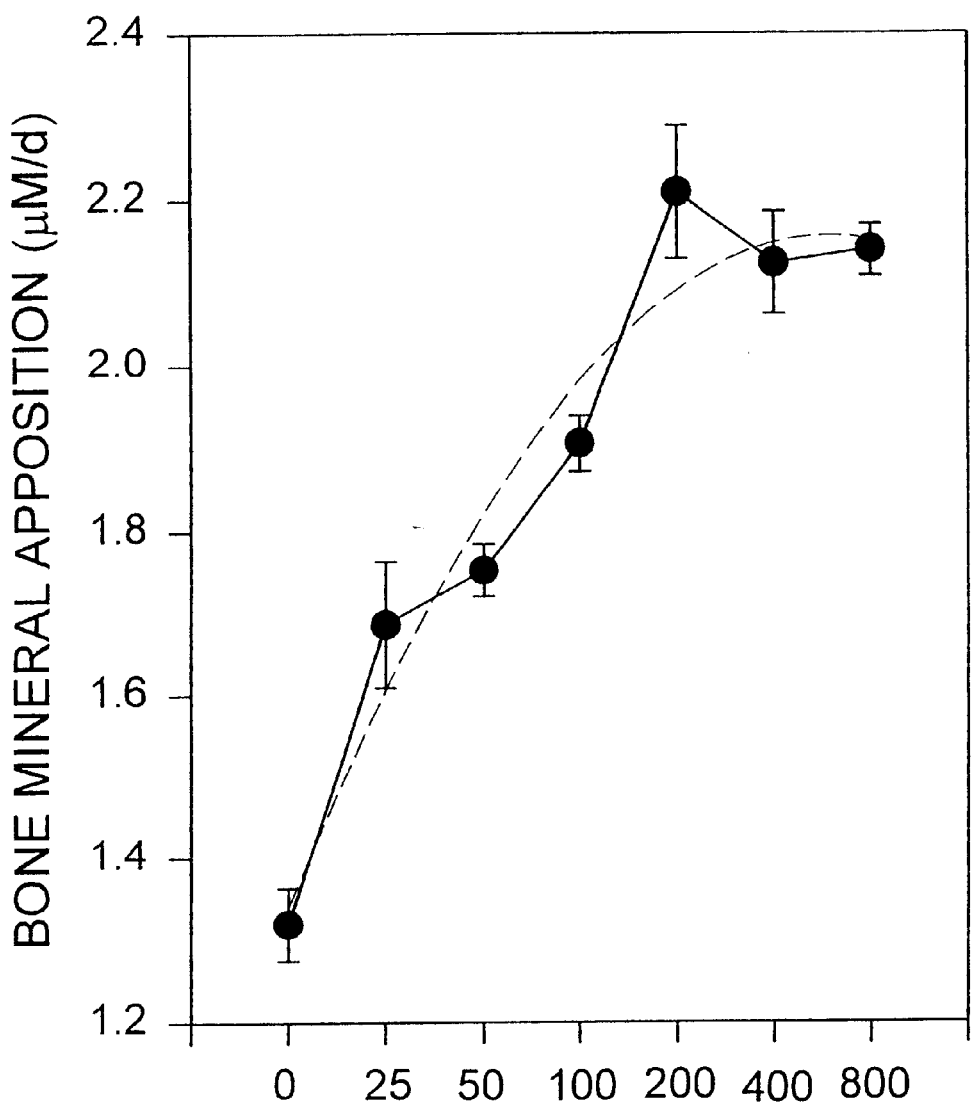
FIG. 4 graphically illustrate the dose dependency of the bone mineral apposition rate ($\mu$m per day) found for rats injected with the indicated amounts of polypeptide having SEQ ID NO:18. The error bars are ±1 S.E.

In a fourth set of experiments, dose dependence of the measured bone mineral apposition rate on the amount of polypeptide having SEQ ID NO:18 was evaluated. Twenty-eight female Sprague-Dawley rats (average weight, about 300 gm) were divided into seven groups of four. The rats were treated as described in the previous set of experiments except that the amount of test polypeptide varied as follows: 25, 50, 100, 200, 400 and 800 nmoles. The results obtained are shown in Table Four and FIG. 4.

TABLE FOUR

Dose Dependency of Bone Apposition Rates (μm/day) on Amount of Polypeptide having SEQ ID NO:18

|  | Control | 25 nmol | 50 nmol | 100 nmol | 200 nmol | 400 nmol | 800 nmol |
|---|---|---|---|---|---|---|---|
| Mean | 1.320 | 1.686 | 1.753 | 1.907 | 2.209 | 2.123 | 2.139 |
| S.E. | 0.04 | 0.08 | 0.03 | 0.03 | 0.08 | 0.06 | 0.03 |
| N | 4 | 4 | 4 | 4 | 4 | 4 | 4 |

As graphically illustrated in FIG. 2, NAP-2V-(1-26) (SEQ ID NO:11) and NAP-2V-(13-26; $gln^{25} \rightarrow glu^{25}$) (SEQ ID NO:12) act to stimulate bone growth, the latter of these two polypeptides displaying greater activity. As illustrated in FIG. 3, NAP-2V-(15-21) having its amino and carboxy termini protected (SEQ ID NO:18) has greater bone stimulatory activity than the similarly protected NAP-2V-(13-26; $gln^{25} \rightarrow glu^{25}$) (SEQ ID NO:17).

NAP-2V-(10-26) (SEQ ID NO:13) appeared to cause a small increase in the observed bone apposition rate, although the significance of the observed increase was questionable. NAP-2V-(11-26) (SEQ ID NO:14) and NAP-2V-(12-26) (SEQ ID NO:15) were found to have no effect on observed bone mineral apposition rate. The sequence of NAP-2V-(10-26) retains both the $cys^{10}$ and $cys^{12}$ residues. The sequences of NAP-2V-(11-26) and NAP-2V-(12-26) each retain the $cys^{12}$ residue. The sequence of NAP-2V-(13-26; $gln^{25} \rightarrow glu^{25}$) retains neither of the $cys^{10}$ and $cys^{12}$ residues. All of these NAP-2V subsequences lack the $cys^{36}$ and $cys^{52}$ residues present in the parent NAP-2V. It may be that the reduced activity of NAP-2V-(10-26), NAP-2V-(11-26) and NAP-2V-(12-26) is due to spontaneous intermolecular disulfide bonding that prevents a polypeptide-receptor interaction required for the bone stimulatory effect, but this is not known for certain.

The sequence of NAP-2V-(13-26; $gln^{25} \rightarrow glu^{25}$) is different from the corresponding subsequence of NAP-2V at the 25 position, a glutamic acid residue being present in place of the glutamine residue. It would of course be expected that the subsequence having the glutamine residue as occurs in NAP-2V would also act to stimulate bone growth in mammals.

It has been postulated that NAP-2 contains two internal disulfide bonds, between Cys-5 and Cys-31, and Cys-7 and Cys-47, respectively (Baggiolini, M., Clemetson, K. J., Walz, A. International Patent Application No. PCT/EP89/01389, published Jun. 14, 1990 under WO90/06321.). By extension, sequences and subsequences disclosed herein that contain the corresponding cysteine residues would likely contain similar linkages therebetween.

It will of course be understood, without the intention of being limited thereby, that a variety of other substitutions of amino acids is possible while preserving the structure responsible for the bone stimulatory effect of the subsequences of NAP-2V disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Preferred substitutions are those which are conservative, i.e., wherein a residue is replaced by another of the same general type. As is well understood, naturally occurring amino acids can be subclassified as acidic, basic, neutral and polar, or neutral and nonpolar. Furthermore, three of the encoded amino acids are aromatic. It is generally preferred that peptides differing from the native sequence contain substitutions which are from the same group as that of the amino acid replaced. Thus, in general, the basic amino acids Lys, Arg, and His are interchangeable; the acidic amino acids aspartic and glutamic are interchangeable; the neutral polar amino acids Ser, Thr, Cys, Gln, and Asn are interchangeable; the non-polar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. A peptide containing an amino acid sequence that can be aligned with that of SEQ ID NO:11, SEQ ID NO:12 or NO:18 and having less than 100% homology therewith may retain at least part of the bone stimulating effect thereof. Of course, it would also be expected that the greater percentage of homology, say 70%, 80%, 90%, or more, could increase the degree of retained bone stimulating activity.

"Sequence identity or homology", as used herein, refers to the sequence similarity between two polypeptide molecules or between two nucleic acid molecules. When a position in both of the two compared polypeptide sequences, for example, is occupied by the same amino acid (for example, if a position in each of two polypeptide molecules is an alanine residue, then the molecules are homologous or sequences are identical at that position. The percent of homology between two molecules or sequence identity between two sequences is a function of the number of such matching positions shared by the two sequences divided by the number of positions compared ×100. For example, if 6 of 10, of the positions in two sequences are the same then the two sequences are 60% homologous or have 60% sequence identity. By way of example, the polypeptide sequences METLIA and MPTWIF share 50% homology or sequence identity. Generally, a comparison is made when two sequences are aligned to give maximum homology.

The comparison of sequences and determination of percent homology between two sequences can be accomplished using a mathematical algorithm. In this specification, the alignment was performed according to two methods, the Clustal method and the J. Hein method. Of these, the Clustal method is preferred.

The Clustal algorithm (as applied here using software available from DNASTAR Inc., 1228 South Park Street, Madison, Wis., USA, 1994) is recommended for aligning sequences whose similarity might not necessarily be evolutionary. The algorithm is described by Higgins, D. G. et al. 1989. *CABIOS* 5:151. The same software programme provides for aligning sequences according to the Jotun Hein method, which is recommended for aligning sequences of highly evolved families that have clear evolutionary relationship. The algorithm is described by Hein, J. 1990. *Methods in Enzymology* 183:626. Programme default settings (standard parameters) were used. In the case of weighting amino acid residues based on evolutionary substitution patterns, charge, structural and chemical similarity, the default PAM250 setting was used. For protein alignments, the pairwise alignment parameters are Ktuple=1, Gap penalty=3, Window=5, and Diagonals Saved=5 were used.

Insofar as deletion of one or more amino acids is concerned, it is likely that deletions of a small number of amino acids from each end of either sequence might be possible, bearing in mind the observation that the deletions to obtain SEQ ID NOs: 14 and 15 yield polypeptides which do not appear to enhance bone growth. Further, symmetrical, or nearly symmetrical deletions would likely be the most possible to be made while retaining the three-dimensional configuration. Internal deletions, although likely to be possible to some limited extent, should be few.

Additions of amino acids could very likely be made at the ends of the sequence, and as with deletions, symmetrical or nearly symmetrical additions to the carboxy and amino terminals are likely to be possible. Internal additions, although likely to be possible to some limited extent, should be few.

Of the above-listed modifications to the sequence, terminal additions are most likely to be most useful, as such a modification can serve a variety of functions: an identifying group as for use in a radioimmunoassay; or a linking group, as examples.

A polypeptide of the present invention can be improved with respect to possible degradation, as might occur in the body in the presence of protease, for instance, by protection of the C-terminus, the N-terminus, or both the C-terminus and N-terminus of the polypeptide.

As used herein, "protected" terminal amino group refers to a terminal amino group (N-terminus) coupled with any of various amino-terminal protecting groups that can be employed in peptide synthesis. Examples of suitable groups include acyl protecting groups, for example, formyl, acetyl, benzoyl, trifluoroacetyl, succinyl, and methoxysuccinyl; aromatic urethane protecting groups, for example benzyloxycarbonyl; and aliphatic urethane protecting groups, for example t-butoxycarbonyl or adamantyloxycarbonyl (Gross and Mienhofer, eds., *The Peptides*, vol 3, pp. 3 to 88 (Academic Press, New York, 1981)).

As used herein, "protected" terminal carboxyl group refers to a terminal carboxyl group (C-terminus) coupled with any of various carboxy-terminal protecting groups. As will be readily apparent to a person skilled in the art, suitable groups include t-butyl, benzyl or other acceptable groups linked to the terminal carboxyl group through an ester or ether bond.

Compounds within the scope of this invention can be synthesized chemically be means well known in the art such, for example, solid phase peptide synthesis. The synthesis is commenced from the carboxy-terminal end of the peptide using an α-amino protected amino acid. t-Butyloxycarbonyl (Boc) protective groups, or other suitable protective groups, can be used (Stewart et al., "Solid-Phase Peptide Synthesis," W.H. Freeman Co., San Francisco (1969); Merrifield, *J. Am. Chem. Soc.* 85:2149–2154 (1963); Vale et al., *Science* 213, 1394–1397 (1981), and Marke et al. *J. Am. Chem. Sci.* 103, 3178 (1981)). Synthetic methods are also described in "Principles of Peptide Synthesis" M. Bodansky Ed. (Spring-Verlag 1984). These and other methods of peptide synthesis are also exemplified by U.S. Pat. Nos. 3,862,925, 3,842,067, 3,972,859, 4,105,602, 4,683,291, 4,244,946 and 4,305,872.

Compounds may also be synthesized using manual or automatic techniques, for example, an Applied BioSystems 430A Peptide Synthesizer (Foster City, Calif.) or a Biosearch SAM 11 automatic peptide synthesizer (Biosearch, Inc., San Rafael, Calif.).

A compound "derived from" a polypeptide having a particular amino acid sequence is any molecular entity which is identical, substantially homologous, or otherwise functionally or structurally equivalent to that polypeptide. Thus, a molecule derived from a particular polypeptide may encompass the amino acid sequence of the polypeptide, any portion of that polypeptide, or other molecular entity that functions to stimulate bone growth. A molecule derived from such a binding domain will mimic the polypeptide from which it is derived. Such molecular entities may include peptide mimetics and the like.

"Peptides mimetics" are structures which serve as substitutes for peptides in interactions with acceptor molecules (see Morgan et al. (1989) *Ann. Reports Med. Chem.* 24:243–252 for a review of peptide mimetics). Peptide mimetics, as used herein, include synthetic structures which may or may not contain amino acids and/or peptide bonds, but retain structural and functional features of a peptide from which they are derived. The term, "peptide mimetics" also includes peptoid and oligopeptoids, which are peptides or oligomers of N-substituted amino acids (Simon et al. (1972) *Proc. Natl. Acad. Sci USA* 89:9367–9371). Further included as peptide mimetics are peptide libraries, which are collections of peptides designed to be a given amino acid length and representing all conceivable sequences of amino acids corresponding thereto.

Two polypeptide sequences are "substantially homologous" when at least about 85% (preferably at least about 85% to 90%, and most preferably at least about 95%) of the nucleotides or amino acids match over a defined length of the polypeptide. As used herein, substantially homologous also refers to sequences showing identity to the specified polypeptide sequence.

Peptide mimetics which structurally and functionally mimic the polypeptides having bone stimulatory activity described herein, will also find use herein and may be generated using the following strategies and procedures. Generally, mimetics are designed based on information obtained by systematic replacement of L-amino acids by D-amino acids, replacement of side chain moieties by a methyl group or pseudoisosteric groups with different electronic properties (see Hruby et al. (1990) Biochem, J. 268:249–262), and by systematic replacement of peptide bonds in the above described peptide inhibitors with amide bond replacements. For example, analogues containing amide bond surrogates may be used to investigate aspects of peptide structure and function, such as rotational freedom in the backbone, intra and intermolecular hydrogen-bond patterns, modifications of local and total polarity and hydrophobicity, and oral bioavailability.

Local conformational constraints can also be introduced to determine conformational requirements for activity of a potential peptide mimetic having bone stimulatory activity. For example, β,β-distributed amino acids may be used to examine the effects of conformational constraints on peptide activity (see, e.g. Manning et al. (1982) J. Med. Chem. 25:408–414; Mosberg et al. (1983) Proc. Natl. Acad. Sci. USA 106:506–512; Pelton et al. (1985) Proc. Natl. Acad. Sci. USA 82:236–239).

The mimetics can include isosteric amide bonds such as ψ[CH$_2$S], ψ[CH$_2$NH], ψ[CNH$_2$], ψ[NHCO], ψ[COCH$_2$] and ψ[(E) or (Z) CH= =CH] see, for review, Spatola (1983) in "Chemistry and Biochemistry of Amino Acids, Peptides and Proteins," Volume VII. (Weinstein ed.), Marcel Dekker, New York, 267–357). The synthetic molecules can also include D-amino acids to stabilize or promote reverse turn conformations and to help stabilize the molecule from enzymatic degradation (see, e.g. Freidinger et al (1985) in "Peptides: Structure and Function." (Deber et al. eds.), Pierce Chem Co., Rockford, Ill., 549–552; Sawyer et al (1980) Proc. Natl. Acad. Sci. USA 77:5754–5758; Torchiana et al (1978) Arch. Int. Pharmacol. Ther. 235:170–176). Cyclic amino acid analogues may be used to constrain amino acid residues to particular conformational states, e.g. αα'- and ββ-substituted cyclic amino acids such as 1-aminocyclopentanccarboxylic acid (cycloleucine) and ββ-cyclopentamethlyene-β-mercaptopropionic acid (see Hruby et al (1990), supra).

The mimetics can also include mimics of polypeptide secondary structure—structures which can model the 3-dimensional orientation of amino acid residues into the known secondary conformations of proteins—including β-turn mimetics, such as phenoxathin ring system, and β-sheet mimics, such as epindolidione structures. Design synthesis and conformational analysis of a α-helix inducing template has been described (Kemp et al (1988) Tetrahedron Lett. 29:4931; Kemp et al. (1988) Tetrahedron Lett. 29:4935).

A potential mimetic can be tested, or pre-screened, for potential activity as a bone stimulating compound by measuring the affinity of the compound for an antibody raised against the polypeptide from which the mimetic is derived. As described above for polypeptides, those mimetics that react positively with the antibody to the already known peptide could then be tested for bone stimulatory effects in vivo using the system described herein for rats, for example. Antibodies raised against a polypeptide having the amino acid sequence identified as SEQ ID NO:9 would be particularly useful in this context.

Peptoids will find use herein. Peptoids are oligomers of N-substituted amino acids (Simon et al (1972), supra). and can be used as motifs for the generation of chemically diverse libraries of novel molecules, which can then be tested for binding and bone stimulatory activity. The monomers may incorporate t-butyl-based side-chain and 9-fluorenylmethoxy-carbonyl α-amine protection. Oligomerization of the peptoid monomers may be performed by for example, in situ activation by either benzotriazol-l-yloxytris(pyrrolidino)phosphonium hexafluorphosphate or bromotris(pyrrolidino)phosphonium hexafluorphosphate. Other steps are identical to conventional peptide synthesis using α-(9-fluorenylmethoxycarbonyl)amino acids. Oligopeptoids may be identified which have affinities comparable to the corresponding polypeptides and, thus, are potentially useful as bone stimulatory agents.

Compounds of the present invention and compositions containing them find use in numerous therapeutic and prophylactic applications in the prevention and treatment of bone reduction related to a disease. Compounds can thus be used as treatments to promote bone growth, in the treatment of osteoporosis, for example, by any suitable route. The preferred routes are suitable for delivery of polypeptide-type compounds to the bloodstream of a subject, bearing in mind proper storage and handling conditions required for polypeptides such as those described herein.

Thus the present invention also provides compositions containing an effective amount of compounds of the present invention, including the nontoxic addition salts, amides and esters thereof, which may, alone, serve to provide the treatment benefits described above. Such compositions can also be provided together with physiologically tolerable liquid, gel or solid diluents, adjuvants and excipients.

In the above examples involving subsequences of NAP-2V, about 75 nmol of polypeptide per kg of bodyweight of animal was used per administration. In practice, particularly as human subjects are concerned, the daily dosage may well be between 0.01 and 300 mg or more per kg of bodyweight. More preferably, the dosage would be in the neighborhood of from about 0.1 to about 30 mg per kg of bodyweight. It may be that the preferred frequency of administration would be greater or less than once per day, depending upon the route of administration, convenience, and the variation of effectiveness of treatment with frequency of and amount used per administration. The dosage administered also depends on the subject and to which effect such administration is to give. The dosage of any one or more of the compounds will depend on many factors including the specific compound or combination of compounds being utilized, the mode of administration, and the mammal being treated. Dosages of a particular compound or combination of compounds can be determined using conventional considerations; for example, by customary comparison of the differential activities of the subject compounds and that of a known agent, that is, by means of an appropriate pharmacological protocol in which, for example, bone density of subjects is measured overtime.

Pharmaceutical preparations include any of the compounds prepared as an injectable solution, including an injectable solution prepared just prior to use, for promoting bone growth and/or treatment of osteoporosis. An injectable can be either a liquid solution or suspension; solid forms suitable for solution in, or suspension in, liquid prior to injection may also be prepared. The preparation may also be emulsified. The active polypeptide is often mixed with diluents and excipients which are physiologically tolerable and compatible with the polypeptide. Suitable diluents and excipients are, for example, water, saline, dextrose, glycerol, or the like, and combinations thereof. In addition, if desired, the compositions can contain minor amounts of auxiliary substances such as wetting or emulsifying agents, stabilizing or pH buffering agents, and the like.

Pharmaceutical preparations include the employment of the compounds in admixture with conventional excipients, that is, pharmaceutically acceptable organic or inorganic carrier substances which do not deleteriously react with the compounds, and which possibly enhance the storage and handling stability of the compounds. The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

The compositions are conventionally administered parenterally, by injection, for example either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills capsules, sustained release formulations, or powders, and contain 10%–95% of active ingredient, preferably 25%–70%. These oral formulations include formulations designed to protect the peptide until it can be absorbed.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The compounds of the invention can be homopolymerized to themselves (i.e., (peptide)$_n$) or, heteropolymerized to one another. The compounds can also be conjugated to biocompatible polymeric compounds, such as BIOPOL™ (WR Grace & Co.-Conn.).

If prepared using recombinant techniques, a DNA sequence encoding a desired polypeptide of the present invention is synthesized using standard automated techniques, or the coding sequences or portions thereof are retrieved from cDNA or genomic libraries. This DNA is ligated into suitable expression vectors and these vectors are transformed into appropriate hosts. A variety of expression vector/host cell systems can be used, including both procaryotic and eukaryotic culture systems.

Procaryotes most frequently are represented by various strains of E. coli. However, other microbial strains may also be used, such as bacilli, for example bacillus subtilis, various species of Pseudomonas, or other bacterial strains. In such procaryotic systems, plasmid vectors which contain replication origins, and control sequences derived from a species compatible with the host are used. For example, E. coli is typically transformed using derivatives of pBR322, a plasmid derived from an E. coli species (Bolivar et al., (1977) Gene 2:95. Commonly used procaryotic control sequences, which are defined herein to include promoters for transcription initiation, optionally with an operator, along with ribosome binding site sequences, include such commonly used promoters as the beta-lactamase (penicillinase), lactose (1 nc) promoter systems (Chang et al., (1977) Nature 198:1056), the tryptophan (trp) promoters system (Goeddel et al., (1990) Nucleic Acids Res 8:4057), and the lambda-derived $P_L$ promoter and N-gene ribosome binding site (Shimatake et al., (1981) Nature 292:128). However, any available promoter system compatible with procaryotes can be used.

The expression systems useful in the eukaryotic systems of the invention comprise promoters derived from appropriate eukaryotic genes. A class of promoters useful in yeast, for example, include promoters for synthesis of glycolytic enzymes, including alcohol dehydrogenase promoters, glyceraldehyde-3-phosphate dehydrogenase promoter (Holland & Holland, (1980) J Biol Chem 25:2596), alpha-factor promoter (Bitter et al., (1984) Proc Natl Acad Sci 81:5330), the gal promoter (Johnston & David, (1984) Mol Cell Biol 4:1440) those for 3-phosphoglycerate kinase (Hitzeman et al., (1980) J. Biol Chem 256:1385) or the Leu2 gene obtained from YEp13 (Broach, J., et al., (1978) Gene 8:121).

Suitable mammalian promoters include the early and late promoters from SV40 (Fiers et al., (1978) Nature 273:113) or other viral promoters such as those derived from polyoma, adenovirus 11, bovine papilloma virus or avian sarcoma viruses. Suitable viral and mammalian enhancers are cited above. In the event plant cells are used as an expression system, the nopaline synthesis promoter is appropriate (Depicker, A., et al., (1982) J Mol Appl Gen 1:56).

The expression systems are included on replication vectors or are caused to integrate into the chromosome of a recombinant host. For systems wherein the vectors include a replication system, these may be low or high copy number, usually having copy numbers of fewer than about 1000, although in certain situations, runaway vectors may be employed. Whether provided on a vector intended for integration or in a replication system, the sequence encoding a polypeptide of the invention may be ligated in tandem with an amplifying gene such as dihydrofolate reductase, metallothioneins, thymidine kinase, or the like. In procaryotic systems, both the amplifying gene and the target gene can be under the regulation of the same transcriptional and translational regulatory regions.

Usually, the vector will include a marker which allows for selection of host cells containing the expression system; the nature of these markers depends on the host and is understood in the art. In addition to required regulators such as promoters, additional sequences such as enhancers can also be employed to enhance the level of transcription. If the polypeptide is to be secreted, an upstream sequence encoding signal peptides such as those described in U.S. Pat. Nos. 4,336,336; 4,338,397; and 4,546,082 may be employed. The signal sequence is enzymatically cleaved as the polypeptide product is secreted.

Depending on the host cell used, transformation is done using standard techniques appropriate to such cells. The calcium treatment employing calcium chloride, as described by Cohen, S. N., (1972) *Proc Natl Acad Sci USA* 69:2110; or the RbCl method described in Maniatis et al., *Molecular Cloning: A Laboratory Manual* (1982) Cold Spring Harbor Press, p. 254 is used for procaryotes or other cells which contain substantial cell wall barriers. Infection with *Agrobacterium tumefaciens* (Shaw, C. H., (1938) et al., *Gene* 23:315) is used for certain plant cells. For mammalian cells without such cell walls, the calcium phosphate precipitation method of Graham and van der Eb, (1978) *Virology* 52:2:546 is preferred. Transformations into yeast are carried out, for example, according to the method of Van Solingen, P., et al., (1977) *J Bacter* 130:946; and Hsiao, C. L., et al., (1979) *Proc Natl Acad Sci USA* 76:3829.

In general, after construction of a suitable expression system, the system is transfected into the appropriate host and successful transformants are selected by markers contained on the expression vectors. Successfully transformed colonies are then cultured in order to produce the desired polypeptide. It is sometimes preferred that a promoter which can be controlled by regulating conditions in the environment be used so that the cells can be grown under conditions where the gene encoding the desired polypeptide of the invention is not expressed, and then production of the polypeptide induced by appropriate manipulation of conditions. For example, if the trp promoter is used in *E. coli*, the cells are grown in the presence of tryptophan and expression is then induced by diminution of tryptophan concentration or by addition of a tryptophan analogue such as indolylacetic acid. If the gene is under control of the PL promoter, the cells are grown at relatively low temperature, such as at about 35° C., to a suitable cell density, and the temperature is then elevated to activate this promoter. If produced in bacterial hosts as a mature intracellular polypeptide, the N-terminal methionine may or may not be cleaved. In mammalian systems, for example, the use of the metallothionein promoter permits induction by addition of heavy metals or glucocorticoids. This protocol is preferred to prevent premature accumulation of the polypeptide which might be harmful to the growth of the cell.

The polypeptide can be produced intracellularly, or in secreted form by construction of vectors in which the peptide is preceded by a signal peptide workable in the appropriate host.

The polypeptide is recovered from the medium or from the cells using suitable techniques generally known in the art, and purified by, for example, ion exchange chromatography, ammonium sulfate precipitation, gel permeation chromatography, and so forth.

The polypeptide made available by the invention disclosed herein can be used to obtain antisera thereto (Stites, D. P. and A. I. Terr. 1991. In Basic & Clinical Immunology, 7th Ed. Appleton and Lange, Norwalk, Conn. and San Matea Calif.). Methodology and products can be developed using an antibody to a polypeptide for use in detecting the polypeptide with which the antibody binds. This apparently having been accomplished at least for the polypeptide having the sequence of CTAP-III (SEQ ID NO:3) (Baggiolini, M., Clemetson, K. J., Walz, A. International Patent Application No. PCT/EP89/01389, published Jun. 14, 1990 under WO90/06321). Methodology and products can be developed using an antibody to a polypeptide for use in detecting the polypeptide with which the antibody binds.

For example, an antibody can be linked to or conjugated with a reporter system which is set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluorescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

A further advantage may be obtained through chimeric forms of the protein, as known in the art. A DNA sequence encoding the entire protein, or a portion of the protein, could thus be linked with a sequence coding for the C-terminal portion of *E. coli* β-galactosidase to produce a fusion protein, for example. An expression system for human respiratory syncytial virus glycoproteins F and G is described in U.S. Pat. No. 5,288,630 issued Feb. 22, 1994 and references cited therein, for example.

All references cited in this specification are incorporated herein by reference, including U.S. Provisional Patent Application Serial No. 004,314 filed Sep. 26, 1995.

I claim the following:

1. An isolated polypeptide which consists essentially of the amino acid sequence identified as SEQ ID NO:1B.

2. A pharmaceutical composition for promoting bone growth, comprising a therapeutically effective amount of the polypeptide of claim 1.

3. An agent for use in prevention and treatment of a bone reduction related disease which corn rises a polypeptide of claim 1 as an active ingredient.

* * * * *

UNITED STATES PATENT AND TRADEMARK OFFICE
CERTIFICATE OF CORRECTION

| | |
|---|---|
| PATENT NO. | : 6,693,081 B2 |
| DATED | : February 17, 2004 |
| INVENTOR(S) | : Tam, Cherk Shing |

Page 1 of 1

It is certified that error appears in the above-identified patent and that said Letters Patent is hereby corrected as shown below:

<u>Column 31,</u>
Line 34, change "1B" to -- 18 --

Signed and Sealed this

Second Day of August, 2005

JON W. DUDAS
*Director of the United States Patent and Trademark Office*

SEQUENCE LISTING

<160> NUMBER OF SEQ ID NOS: 19

<210> SEQ ID NO 1
<211> LENGTH: 70
<212> TYPE: PRT
<213> ORGANISM: Artificial Sequence
<220> FEATURE:
<223> OTHER INFORMATION: Description of Artificial Sequence: Chemically synthesized polypeptide

<400> SEQUENCE: 1

Ala Glu Leu Arg Cys Met Cys Ile Lys Thr Thr Ser Gly Ile His Pro
1               5                   10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser Ala Asp
65                  70

<210> SEQ ID NO 2
<211> LENGTH: 75
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 2

Asp Ser Asp Leu Tyr Ala Glu Leu Arg Cys Met Cys Ile Lys Thr Thr
1               5                   10                  15

Ser Gly Ile His Pro Lys Asn Ile Gln Ser Leu Glu Val Ile Gly Lys
            20                  25                  30

Gly Thr His Cys Asn Gln Val Glu Val Ile Ala Thr Leu Lys Asp Gly
        35                  40                  45

Arg Lys Ile Cys Leu Asp Pro Asp Ala Pro Arg Ile Lys Lys Ile Val
    50                  55                  60

Gln Lys Lys Leu Ala Gly Asp Glu Ser Ala Asp
65                  70                  75

<210> SEQ ID NO 3
<211> LENGTH: 74
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 3

Ser Asp Leu Tyr Ala Glu Leu Arg Cys Met Cys Ile Lys Thr Thr Ser
1               5                   10                  15

Gly Ile His Pro Lys Asn Ile Gln Ser Leu Glu Val Ile Gly Lys Gly
            20                  25                  30

Thr His Cys Asn Gln Val Glu Val Ile Ala Thr Leu Lys Asp Gly Arg
        35                  40                  45

Lys Ile Cys Leu Asp Pro Asp Ala Pro Arg Ile Lys Lys Ile Val Gln
    50                  55                  60

Lys Lys Leu Ala Gly Asp Glu Ser Ala Asp
65                  70

<210> SEQ ID NO 4
<211> LENGTH: 73
<212> TYPE: PRT
<213> ORGANISM: Artificial Sequence
<220> FEATURE:
<223> OTHER INFORMATION: Description of Artificial Sequence: Chemically
      synthesized polypeptide

```
<400> SEQUENCE: 4

Asp Leu Tyr Ala Glu Leu Arg Cys Met Cys Ile Lys Thr Thr Ser Gly
  1               5                  10                  15

Ile His Pro Lys Asn Ile Gln Ser Leu Glu Val Ile Gly Lys Gly Thr
             20                  25                  30

His Cys Asn Gln Val Glu Val Ile Ala Thr Leu Lys Asp Gly Arg Lys
         35                  40                  45

Ile Cys Leu Asp Pro Asp Ala Pro Arg Ile Lys Lys Ile Val Gln Lys
     50                  55                  60

Lys Leu Ala Gly Asp Glu Ser Ala Asp
 65                  70

<210> SEQ ID NO 5
<211> LENGTH: 81
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 5

Gly Lys Glu Glu Ser Leu Asp Ser Asp Leu Tyr Ala Glu Leu Arg Cys
  1               5                  10                  15

Met Cys Ile Lys Thr Thr Ser Gly Ile His Pro Lys Asn Ile Gln Ser
             20                  25                  30

Leu Glu Val Ile Gly Lys Gly Thr His Cys Asn Gln Val Glu Val Ile
         35                  40                  45

Ala Thr Leu Lys Asp Gly Arg Lys Ile Cys Leu Asp Pro Asp Ala Pro
     50                  55                  60

Arg Ile Lys Lys Ile Val Gln Lys Lys Leu Ala Gly Asp Glu Ser Ala
 65                  70                  75                  80

Asp

<210> SEQ ID NO 6
<211> LENGTH: 85
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 6

Asn Leu Ala Lys Gly Lys Glu Glu Ser Leu Asp Ser Asp Leu Tyr Ala
  1               5                  10                  15

Glu Leu Arg Cys Met Cys Ile Lys Thr Thr Ser Gly Ile His Pro Lys
             20                  25                  30

Asn Ile Gln Ser Leu Glu Val Ile Gly Lys Gly Thr His Cys Asn Gln
         35                  40                  45

Val Glu Val Ile Ala Thr Leu Lys Asp Gly Arg Lys Ile Cys Leu Asp
     50                  55                  60

Pro Asp Ala Pro Arg Ile Lys Lys Ile Val Gln Lys Lys Leu Ala Gly
 65                  70                  75                  80

Asp Glu Ser Ala Asp
             85

<210> SEQ ID NO 7
<211> LENGTH: 94
<212> TYPE: PRT
```

<213> ORGANISM: Artificial Sequence
<220> FEATURE:
<223> OTHER INFORMATION: Description of Artificial Sequence: Chemically synthesized polypeptide

<400> SEQUENCE: 7

```
Ser Ser Thr Lys Gly Gln Thr Lys Arg Asn Leu Ala Lys Gly Lys Glu
 1               5                  10                  15
Glu Ser Leu Asp Ser Asp Leu Tyr Ala Glu Leu Arg Cys Met Cys Ile
            20                  25                  30
Lys Thr Thr Ser Gly Ile His Pro Lys Asn Ile Gln Ser Leu Glu Val
        35                  40                  45
Ile Gly Lys Gly Thr His Cys Asn Gln Val Glu Val Ile Ala Thr Leu
    50                  55                  60
Lys Asp Gly Arg Lys Ile Cys Leu Asp Pro Asp Ala Pro Arg Ile Lys
65                  70                  75                  80
Lys Ile Val Gln Lys Lys Leu Ala Gly Asp Glu Ser Ala Asp
                85                  90
```

<210> SEQ ID NO 8
<211> LENGTH: 79
<212> TYPE: PRT
<213> ORGANISM: Homo sapiens

<400> SEQUENCE: 8

```
Glu Gly Ala Val Leu Pro Arg Ser Ala Lys Glu Leu Arg Cys Gln Cys
 1               5                  10                  15
Ile Lys Thr Tyr Ser Lys Pro Phe His Pro Lys Phe Ile Lys Glu Leu
            20                  25                  30
Arg Val Ile Glu Ser Gly Pro His Cys Ala Asn Thr Glu Ile Ile Val
        35                  40                  45
Lys Leu Ser Asp Gly Arg Glu Leu Cys Leu Asp Pro Lys Glu Asn Trp
    50                  55                  60
Val Gln Arg Val Val Glu Lys Phe Leu Lys Arg Ala Glu Asn Ser
65                  70                  75
```

<210> SEQ ID NO 9
<211> LENGTH: 103
<212> TYPE: PRT
<213> ORGANISM: Porcine

<400> SEQUENCE: 9

```
Met Thr Ser Lys Leu Ala Val Ala Phe Leu Ala Val Phe Leu Leu Ser
 1               5                  10                  15
Ala Ala Leu Cys Glu Ala Asp Val Leu Ala Arg Val Ser Ala Glu Leu
            20                  25                  30
Arg Cys Gln Cys Ile Asn Thr His Ser Thr Pro Phe His Pro Lys Phe
        35                  40                  45
Ile Lys Glu Leu Arg Val Ile Glu Ser Gly Phe His Cys Glu Asn Ser
    50                  55                  60
Glu Ile Ile Val Lys Leu Val Asn Gly Lys Glu Val Cys Leu Asp Pro
65                  70                  75                  80
Lys Glu Lys Trp Val Gln Lys Val Val Gln Ile Phe Leu Lys Arg Thr
                85                  90                  95
Glu Lys Gln Gln Gln Gln Gln
            100
```

<210> SEQ ID NO 10

```
<211> LENGTH: 70
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 10

Glu Ala Glu Glu Asp Gly Asp Leu Gln Cys Leu Cys Val Lys Thr Thr
 1               5                  10                  15

Ser Gln Val Arg Pro Arg His Ile Thr Ser Leu Glu Val Ile Lys Ala
            20                  25                  30

Gln Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
 65                  70

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 11

Asp Ser Asp Leu Tyr Ala Glu Leu Arg Cys Met Cys Ile Lys Thr Thr
 1               5                  10                  15

Ser Gly Ile His Pro Lys Asn Ile Gln Ser
            20                  25

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 12

Ile Lys Thr Thr Ser Gly Ile His Pro Lys Asn Ile Glu Ser
 1               5                  10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 13

Cys Met Cys Ile Lys Thr Thr Ser Gly Ile His Pro Lys Asn Ile Gln
 1               5                  10                  15

Ser

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Chemically
      synthesized polypeptide
```

```
<400> SEQUENCE: 14

Met Cys Ile Lys Thr Thr Ser Gln Ile His Pro Lys Asn Ile Gln Ser
  1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 15

Cys Ile Lys Thr Thr Ser Gly Ile His Pro Lys Asn Ile Gln Ser
  1               5                  10                  15

<210> SEQ ID NO 16
<211> LENGTH: 228
<212> TYPE: DNA
<213> ORGANISM: Artificial Sequence
<220> FEATURE:
<221> NAME/KEY: CDS
<222> LOCATION: (1)..(225)
<220> FEATURE:
<223> OTHER INFORMATION: Description of Artificial Sequence: Chemically
      synthesized nucleic acid

<400> SEQUENCE: 16 gac agt gac ttg tat gct gaa ctc cgc tgc atg tgt ata aag aca acc        48
Asp Ser Asp Leu Tyr Ala Glu Leu Arg Cys Met Cys Ile Lys Thr Thr
  1               5                  10                  15 tct gga att cat ccc aaa aac atc caa agt ttg gaa gtg atc ggg aaa        96
Ser Gly Ile His Pro Lys Asn Ile Gln Ser Leu Glu Val Ile Gly Lys
                 20                  25                  30 gga acc cat tgc aac caa gtc gaa gtc ata gcc aca ctg aag gat ggg       144
Gly Thr His Cys Asn Gln Val Glu Val Ile Ala Thr Leu Lys Asp Gly
             35                  40                  45 agg aaa atc tgc ctg gac cca gat gct ccc aga atc aag aaa att gta       192
Arg Lys Ile Cys Leu Asp Pro Asp Ala Pro Arg Ile Lys Lys Ile Val
         50                  55                  60 cag aaa aaa ttg gca ggt gat gaa tct gct gat taa                       228
Gln Lys Lys Leu Ala Gly Asp Glu Ser Ala Asp
 65                  70                  75

<210> SEQ ID NO 17
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is N-acetyl isoleucine
<220> FEATURE:
<221> NAME/KEY: MOD_RES
<222> LOCATION: (14)
<223> OTHER INFORMATION: Xaa is serinamide
<220> FEATURE:
<223> OTHER INFORMATION: Description of Artificial Sequence: Chemically
      synthesized polypeptide

<400> SEQUENCE: 17

Xaa Lys Thr Thr Ser Gly Ile His Pro Lys Asn Ile Glu Xaa
  1               5                  10

<210> SEQ ID NO 18
<211> LENGTH: 8
```

```
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is N-acetyl threonine
<220> FEATURE:
<221> NAME/KEY: MOD_RES
<222> LOCATION: (8)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 18

Xaa Thr Ser Gly Ile His Pro Xaa
  1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 19

Thr Thr Ser Gly Ile His Pro Lys
  1               5
```